(12) United States Patent
Wan et al.

(10) Patent No.: US 11,793,434 B1
(45) Date of Patent: Oct. 24, 2023

(54) SYSTEM TO PERFORM VISUAL RECOGNITION AND VEHICLE ADAPTATION

(71) Applicant: GM Global Technology Operations LLC, Detroit, MI (US)

(72) Inventors: Jingyan Wan, Sterling Heights, MI (US); Ke Liu, Lexington, MA (US); Omer Tsimhoni, Bloomfield Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 17/747,449

(22) Filed: May 18, 2022

(51) Int. Cl.
*A61B 5/16* (2006.01)
*A61B 5/18* (2006.01)
*A61B 5/00* (2006.01)
*B60K 35/00* (2006.01)

(52) U.S. Cl.
CPC .............. *A61B 5/165* (2013.01); *A61B 5/18* (2013.01); *A61B 5/6893* (2013.01); *B60K 35/00* (2013.01); *B60K 2370/149* (2019.05); *B60K 2370/1529* (2019.05); *B60K 2370/193* (2019.05)

(58) Field of Classification Search
CPC ......... A61B 5/165; A61B 5/18; A61B 5/6893; B60K 35/00; B60K 2370/1529; B60K 2370/149; B60K 2370/193
USPC ........................................................ 340/576
See application file for complete search history.

(56) References Cited

U.S. PATENT DOCUMENTS

| | | | | |
|---|---|---|---|---|
| 9,465,978 | B2 * | 10/2016 | Hachisuka | A61B 5/7405 |
| 10,067,341 | B1 * | 9/2018 | Breed | G06V 20/597 |
| 10,185,392 | B2 * | 1/2019 | Mueller | G06F 3/147 |
| 10,185,395 | B2 * | 1/2019 | Nagasaki | A61B 5/1122 |
| 10,296,083 | B2 * | 5/2019 | Sung | G06F 3/1431 |
| 2014/0070934 | A1 * | 3/2014 | Chau | B60K 37/00 340/438 |
| 2014/0350431 | A1 * | 11/2014 | Hagedorn | A61B 5/4836 600/15 |
| 2018/0052458 | A1 * | 2/2018 | Tsuji | B60W 10/06 |
| 2018/0215395 | A1 * | 8/2018 | Keany | G06F 18/22 |
| 2018/0264941 | A1 * | 9/2018 | Sato | B60Q 1/535 |
| 2018/0362053 | A1 * | 12/2018 | Isa | G02B 27/00 |
| 2019/0155279 | A1 * | 5/2019 | Tayama | G05D 1/0061 |
| 2020/0164812 | A1 * | 5/2020 | Chou | G02B 27/0955 |
| 2020/0247425 | A1 * | 8/2020 | Chou | A61B 5/245 |
| 2020/0290630 | A1 * | 9/2020 | Elwart | B60W 40/08 |

(Continued)

OTHER PUBLICATIONS

Palazzo, S. et al., "Decoding Brain Representations by Multimodal Learning of Neural Activity and Visual Features," in IEEE Transactions on Pattern Analysis and Machine Intelligence, vol. 43, No. 11, pp. 3833-3849, Nov. 1, 2021.

(Continued)

*Primary Examiner* — Zhen Y Wu
(74) *Attorney, Agent, or Firm* — Vivacqua Crane PLLC (57) ABSTRACT

A system for interfacing a motor vehicle with a person residing in the motor vehicle incudes a monitor that determines the mental state of the person, a module that receives information from the monitor to provide an addition channel to interface between the motor vehicle and the person, and a module that receives information from the monitor to adapt the motor vehicle according to the mental state of the person to enable the system to execute operations based on the mental state of the person.

19 Claims, 7 Drawing Sheets

(56) References Cited

U.S. PATENT DOCUMENTS

2020/0310538 A1\* 10/2020 Lee .................. A61B 5/375
2020/0317053 A1\* 10/2020 Kikuchi ............ G02B 27/01
2021/0393206 A1\* 12/2021 Kusanagi .......... G06F 3/14

OTHER PUBLICATIONS

Spamipinato, C. et al., "Deep Learning Human Mind for Automated Visual Classification," 2017 IEEE Conference on Computer Vision and Pattern Recognition (CVPR), 2017, pp. 6809-6817.

\* cited by examiner

SYSTEM TO PERFORM VISUAL RECOGNITION AND VEHICLE ADAPTATION

INTRODUCTION

The present disclosure relates to visual displays in a motor vehicle. More specifically, the present disclosure relates to visual recognition and vehicle adaptation based on the images on a display.

Many vehicles provide a display for a driver to obtain information, for example, on a head-up display (HUD) or an in-vehicle display. In some situations, issues concerning the effectiveness of HUDs, such as object-road overlap, have a significant impact. Interference between the actual driving environment and the displayed information can lead to distractions/attention narrowing. For information displayed on the display which does not require driver/rider's direct response (e.g., braking), it is hard to tell if the information has been seen. Also, a rider sitting in the motor vehicle may have difficulty accessing the controls on an in-vehicle display if the display is far from the rider's seat of if the rider has certain motor disabilities of neuromuscular disorders.

Thus, while current in-vehicle displays and HUDs achieve their intended purpose, there is a need for a new and improved system and method for displaying images on an in-vehicle display and on a HUD.

SUMMARY

According to several aspects, a system for interfacing a motor vehicle with a person residing in the motor vehicle incudes a monitor that determines the mental state of the person, a module that receives information from the monitor to provide an addition channel to interface between the motor vehicle and the person, and a module that receives information from the monitor to adapt the motor vehicle according to the mental state of the person to enable the system to execute operations based on the mental state of the person.

In an additional aspect of the present disclosure, the monitor determines if the person is looking at a head-up display (HUD) or looking at information on the HUD.

In another aspect of the present disclosure, the system differentiates what the person sees and does not see on the HUD, or even looking at the HUD.

In another aspect of the present disclosure, the system recognizes that the person has seen information on the HUD and replaces the information with other useful information on the HUD and a screen display.

In another aspect of the present disclosure, the system enables the person to access controls on the screen display or the HUD by looking at the HUD or the screen display.

In another aspect of the present disclosure, the system monitors the fatigue of the person.

In another aspect of the present disclosure, the system monitors the fatigue of the person by determining the person's visual focus strength and duration.

In another aspect of the present disclosure, the system is integrated into a headpiece.

In another aspect of the present disclosure, the headpiece is a headphone, a cap, in a headrest of a seat, or in the seat itself.

In another aspect of the present disclosure, the system provides visual, auditory or tactile information to the person.

According to several aspects, a method for interfacing a motor vehicle with a person residing in the motor vehicle includes one or more of the following: determining the mental state of the person with a monitor; receiving information from the monitor to provide an addition channel to interface between the motor vehicle and the person; and receiving information from the monitor to adapt the motor vehicle according to the mental state of the person to enable the system to execute operations based on the mental state of the person.

In another aspect of the present disclosure, the method further includes determining if the person is looking at a head-up display (HUD) or information on the HUD.

In another aspect of the present disclosure, the method further includes differentiating what the person sees and does not see on the HUD, or even looking at the HUD.

In another aspect of the present disclosure, the method further includes recognizing that the person has seen information on the HUD and replaces the information with other useful information on the HUD and a screen display.

In another aspect of the present disclosure, the method further includes enabling the person to access controls on the screen display or the HUD by looking at the HUD or the screen display.

In another aspect of the present disclosure, the method further includes monitoring the fatigue of the person.

In another aspect of the present disclosure, the fatigue of the person is determined by the visual focus strength and duration of the person.

In another aspect of the present disclosure, the monitor is integrated into a headpiece.

In another aspect of the present disclosure, the headpiece is a headphone, a cap or a headrest.

According to several aspects, a system for interfacing a motor vehicle with a person residing in the motor vehicle includes a monitor that determines the mental state of the person, the monitor determining if the person is looking at a head-up display (HUD) to enable the person to access controls on a screen display or the HUD by looking at the HUD or the screen display, a module that receives information from the monitor to provide an addition channel to interface between the motor vehicle and the person; and a module that receives information from the monitor to adapt the motor vehicle according to the mental state of the person to enable the system to execute operations based on the mental state of the person. The system provides visual, auditory or tactile information to the person.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
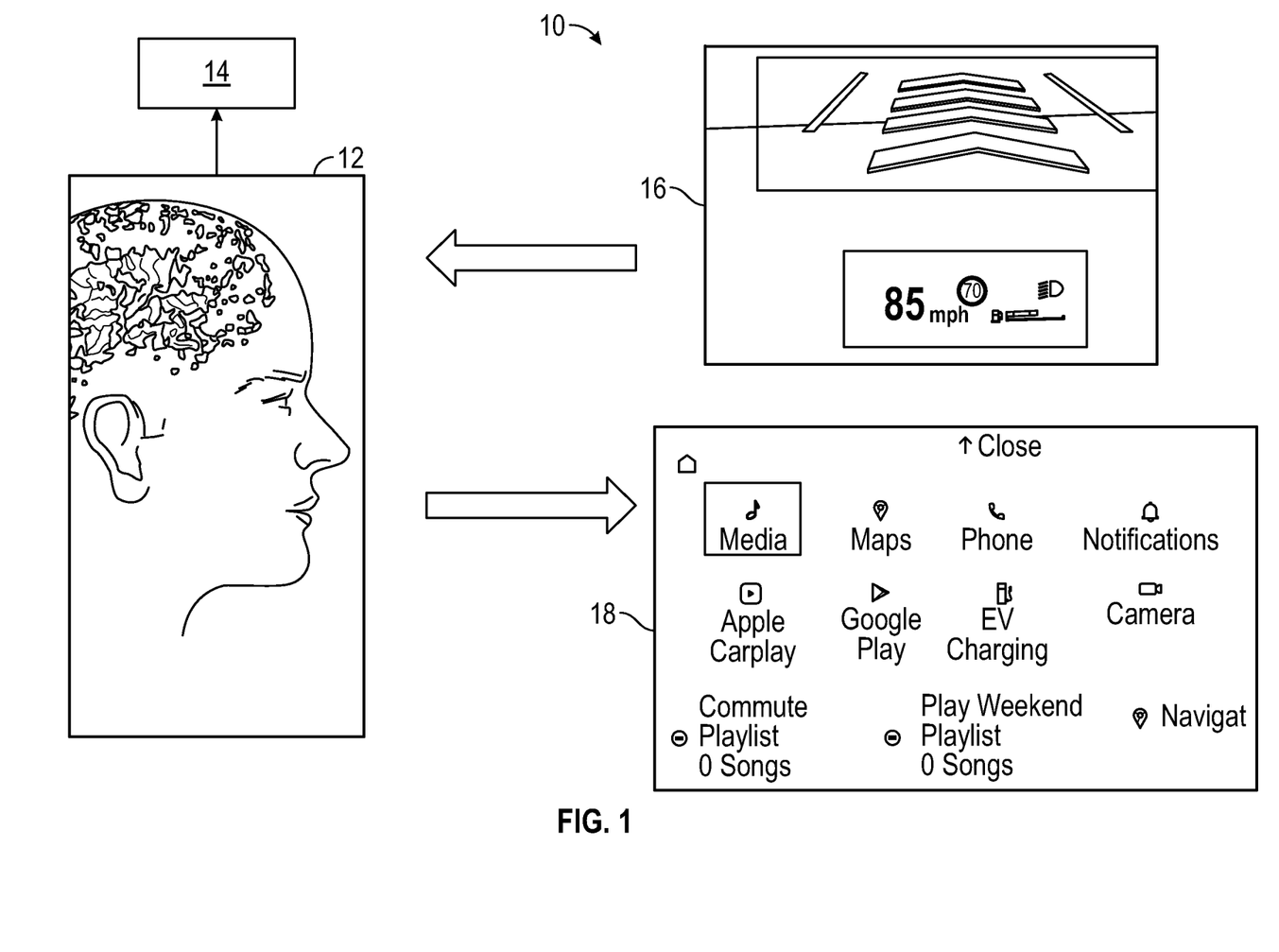
FIG. 1 is an overview diagram of a system to perform visual recognition and vehicle adaptation in accordance with an exemplary embodiment.

Referring to FIG. 1, there is shown a system 10 for interfacing with a driver such as a person 12 residing in a motor vehicle. In some arrangements, the person 12 sees or views a head-up display (HUD) 16 and a mental state 14 of the person 12 is determined. Then through a brain-computer interface (BCI), the person interacts with an in-vehicle display 18. Additionally, or alternatively, the person interacts with the HUD 16. In some arrangements, the BCI infers what the person is looking at.

Figure 2:
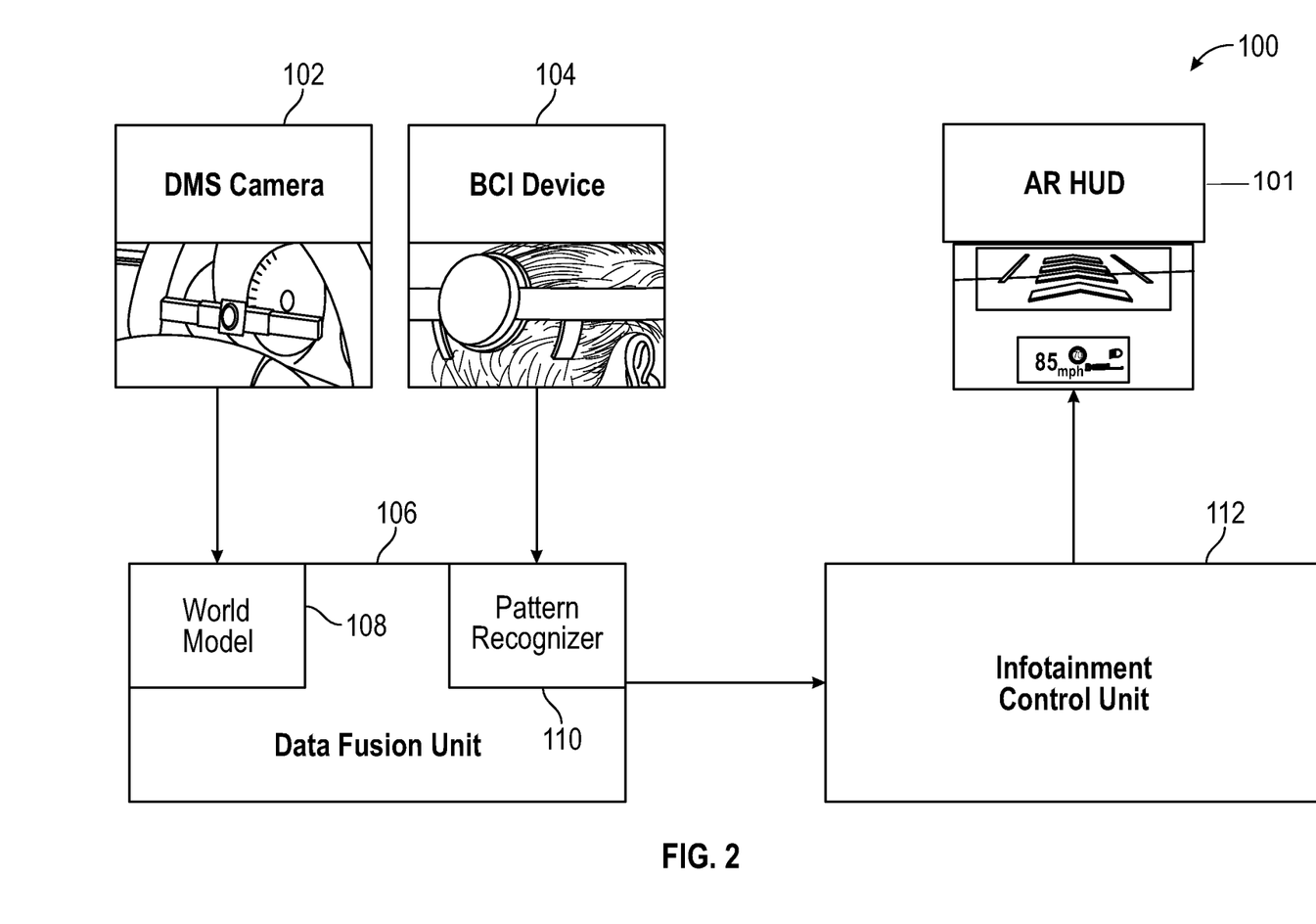
FIG. 2 is a more detailed view of the system show in FIG. 1 in accordance with an exemplary embodiment.

Referring further to FIG. 2, there is shown a more detailed system 100 for interfacing a person with a motor vehicle. Specifically, a driver monitoring system 102 collects data on where the person is looking. A BCI or monitor 104 collects data on what the person is seeing, such as, for example, unique patterns. A world model 108 of a data fusion unit 106 identifies when the person is looking in the vicinity of a HUD 101. A pattern recognizer 110 of the data fusion unit 106 identifies when the person sees a tagged pattern (either from a library of patterns or past history of patterns). The data fusion unit integrates the recognized patterns with where the person is looking. An infotainment control unit controls information on the HUD 101 and applies adaptive algorithms.

The data fusion unit 106 and the infotainment unit 112 includes one or more electronic control units (ECU). The ECU is a non-generalized, electronic control device having a preprogrammed digital computer or processor, memory or non-transitory computer readable medium used to store data such as control logic, software applications, instructions, computer code, data, lookup tables, etc., and a transceiver. Computer readable medium includes any type of medium capable of being accessed by a computer, such as read only memory (ROM), random access memory (RAM), a hard disk drive, a compact disc (CD), a digital video disc (DVD), or any other type of memory. A non-transitory computer readable medium includes media where data can be permanently stored and media where data can be stored and later overwritten, such as a rewritable optical disc or an erasable memory device. Computer code includes any type of program code, including source code, object code, and executable code. The ECU is configured to execute the code or instructions. The ECU may be a dedicated Wi-Fi controller or an engine control module, a transmission control module, a body control module, an infotainment control module, etc. The transceiver is configured to wirelessly communicate, for example, with a hotspot using Wi-Fi protocols under IEEE 802.11x.

The ECU includes one or more application, which is a software program configured to perform a specific function or set of functions. The application may include one or more computer programs, software components, sets of instructions, procedures, functions, objects, classes, instances, related data, or a portion thereof adapted for implementation in a suitable computer readable program code. The applications may be stored within the memory or in additional or separate memory.

The system 100 is based on BCI and DMS that recognizes the information a person sees (e.g., graphics on the HUD 101 or in-vehicle display) and allows: executing operations by visually focusing on the displayed operations employing BCI; and when certain information on the HUD 101 has been seen, that information becomes adaptive.

The system 100 recognizes if a person is looking at information displayed on the HUD 101 or at an external object when they spatially overlap; identifies if the person sees the displayed information or "looks but doesn't see" even with a relatively short glance; and allows the person to access controls on in-vehicle displays, such as, the display 18 shown in FIG. 1 by simply looking at and focusing on the display 18.

The system 100 recognizes different information shown at overlapped or close locations and/or on different places along the direction of gaze: HUD/road, dashboard/steering wheel, fully/partially overlapped information on the same display, etc.

The system 100 recognizes information even if its location changes on the display. The system 100 recognizes the same information in different applications or in different versions of an application.

The system 100 provides adaptive display, that is, after the system 100 recognizes that the person has seen the information displayed on the HUD 100 or the in-vehicle display, such as, the infotainment control unit 112, that information is removed or replaced by other information. If information has not been seen for a certain period or a certain times, it can be displayed in a more salient way (e.g., bigger size) in the future. Further, the system 100 adjusts the timing of notifications if the driver does not respond correctly after the system recognizes that the driver has seen the displayed information. As such, the corresponding notification can be issued earlier. The system 100 further provides control infotainment system though visual focus that enables the person to access controls on in-vehicle displays 112 by simply looking at and focusing on it.

The system 100 also provides early detection of monitor fatigue and sends out notifications when fatigue level is high. The system 100 incorporates eye tracking data as another source of input, especially when the size of information is small, when the information locates close to other information, or when the gaze time is short.

The BCI of the system 100 is employed to identify when the person is actively visually focused on an item. When two objects overlap and the person is focusing on one of them, the system 100 is able to determine which object the person is visually focusing.

As an example, the system 100 tags a visual object and employs electric signals from the person's visual cortex, so when the system 100 determines the person is seeing an object, the system 100 decodes the brain activity of the person and recognizes the active visual focus of the person for adaptive infotainment. Further, the system 100 decodes the brain activity of the person and recognizes the active visual focus for a specific time period for executing a command.

As stated above, the system 100 is able to evaluate the person's fatigue level. Specifically, for a command which requires continuous visual focus strength level higher than L(L∈[0,1]) for a duration T, the person's fatigue level f is calculated as:

$$f = \frac{t-T}{1-L} \cdot \frac{L}{T}$$

where l is the average strength level of the person's visual focus during T, l∈[L,1], l is assessed b the BCI device 104, and t is the time to complete the command execution t∈[T, ∞]. Accordingly, the person takes a break when f is higher than the threshold of the fatigue level in the task.

Figure 3:
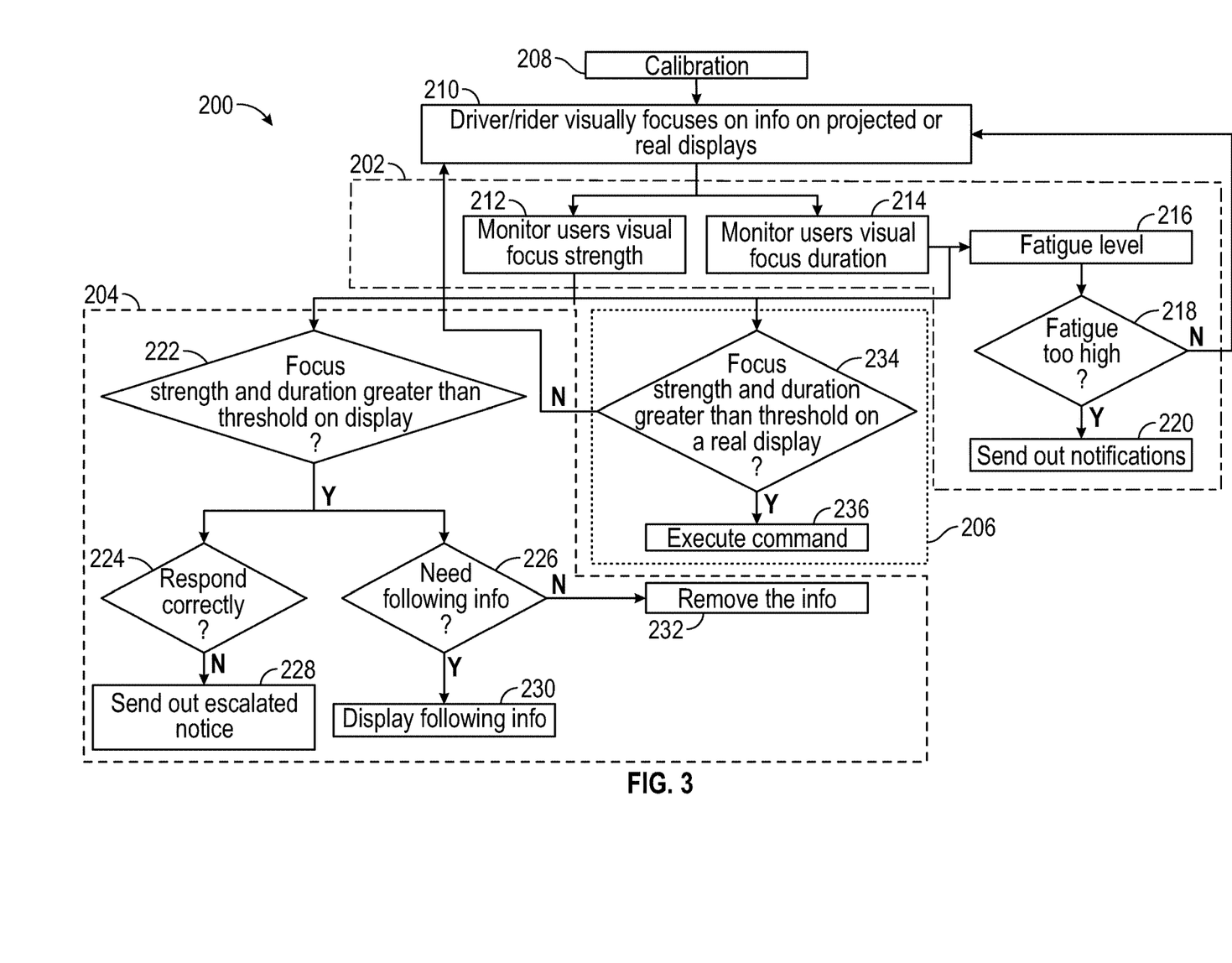
FIG. 3 is a diagram of a process to implement the system shown in FIG. 2 in accordance with an exemplary embodiment.

Referring now to FIG. 3, there is shown a process 200 for implementing the system 100. The system 100 includes a mental state monitoring component 202, a vehicle adaptation component 204, and a component 206 to generate additional human-computer interaction channels.

The process 200 initiates with calibration step 208 and in a step 210 the person visually focuses on information on a projected or a real display. In step 212, the system 100 monitors the person's visual focus strength, in step 214, the system 100 monitors the person's visual focus duration.

In step 216, the system 100 determines the fatigue level of the person, and, in step 218, the system 100 determines if the fatigue level is too high. If the fatigue level is not too high, the process 200 returns to step 210. If the fatigue level is too high, the process 200 proceeds to step 220 and sends out a notification.

From the mental state monitoring component 202, the process 200 further proceeds to the component 206, where a decision step 234 determines if the focus strength and duration are greater than a threshold. If the decision from the step 234 is yes, the process 200 executes a command in step 236. If the decision is no, the process 200 returns to step 210.

The process 200 also proceeds to the component 204, where a decision step 222 determines if the focus strength and duration are greater than a threshold. If the decision is yes, the process proceeds to two additional decision steps 224 and 226. In step 224, the process 200 decides if the response is correct. If the response is not correct, the process 200 sends out a notice in step 228. In step 226, the process 200 determines if it needs the information. If the decision is yes, the process 200 displays the information in step 228, and, if the decision is no, the process 200 removes the information in step 230.

In sum, the system 100 is able to recognize different information shown at overlapped locations or at close locations on the display or on different places on the direction of gaze: information (e.g., warning, notification) displayed on the HUD 101 or looking at outside of the vehicle when the person is looking at the direction of the HUD 101.

The system 100 is able to recognize if the person sees an information or "looks but does not see." The system 100 is able to replace the information which has been seen with other useful information on the in-vehicle display 112, which provides adaptation to the existing infotainment system. The system 100 is able to send out escalated notifications in multimodalities (visual, auditory, tactile, etc.) if the person does not behave correctly after seeing information on the in-vehicle display 112.

The system 100 enables the person to access controls on in-vehicle displays 112 by simply looking at and focusing on it. Note that in-vehicle displays includes projected display (e.g., HUD) and screen displays. Further note, that the person's "controls" include buttons, scroll bars, etc. which can be manipulated by the finger, as well as gesture control and brain control.

The system 100 is able to work with DMS and vehicle sensors to obtain more comprehensive visual focus information.

As stated earlier, the system 100 is able to monitor user fatigue and conduct early detection of fatigue via visual focus strength and duration. The system 100 sends out multimodal notifications (visual, auditory, tactile, etc.) once the user fatigue level is higher than the threshold.

The BCI device 104 in various arrangements is integrated into a head piece such as a headphone, a cap, a headrest.

The system 100 in various arrangements is implemented in traditional human-driven vehicles, autonomous vehicles, and other mental demanding tasks such as AV fleet control, VR games, etc.

Figure 4A:
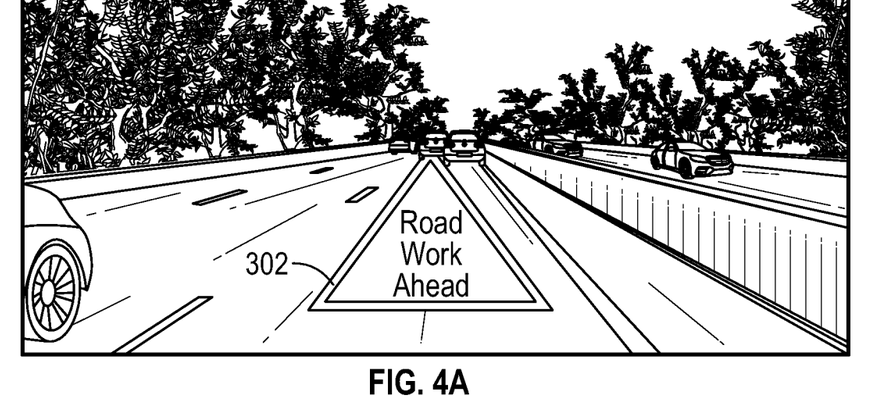
FIG. 4A illustrates a visual of a warning on a HUD generated by the system shown in FIG. 2 in accordance with an exemplary embodiment.
Figure 4B:
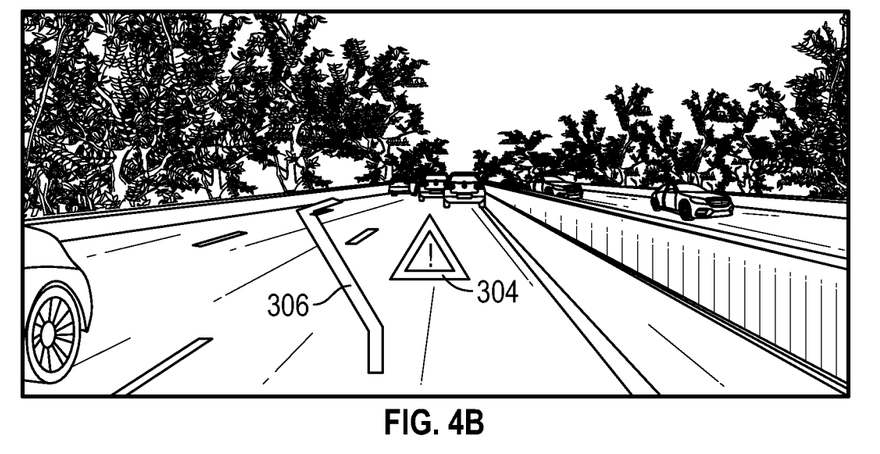
FIG. 4B illustrates a visual on the HUD generated by the system shown in FIG. 2 suggesting an alternative path in accordance with an exemplary embodiment.
Figure 4C:
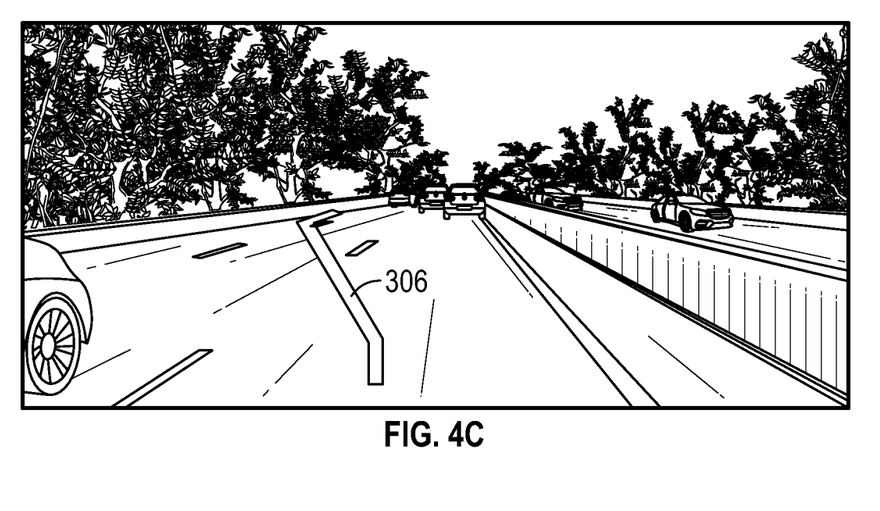
FIG. 4C illustrates the removal of the warning visual from FIG. 4A in accordance with an exemplary embodiment.

Referring now to FIGS. 4A-4C, the figures illustrate how the system 100 provides adaptive information on a HUD. In FIG. 4A, a road work ahead visual 302 is displayed o the HUD 101. In FIG. 4B, after the system 100 recognizes that the person 12 has seen the visual 302, the system 100 navigation activates to provide a path 306 and the visual 302 is minimized. In FIG. 4C, after the system 100 recognizes that the vehicle is head in the correct directions, the visual for the path 306 remains on the HUD 101, while the visual 302 is removed. If the person 12 does not navigate the vehicle as suggested by the system 100, a notification, such as, for example, an auditory warning is sent to the person 12.

Figure 5A:
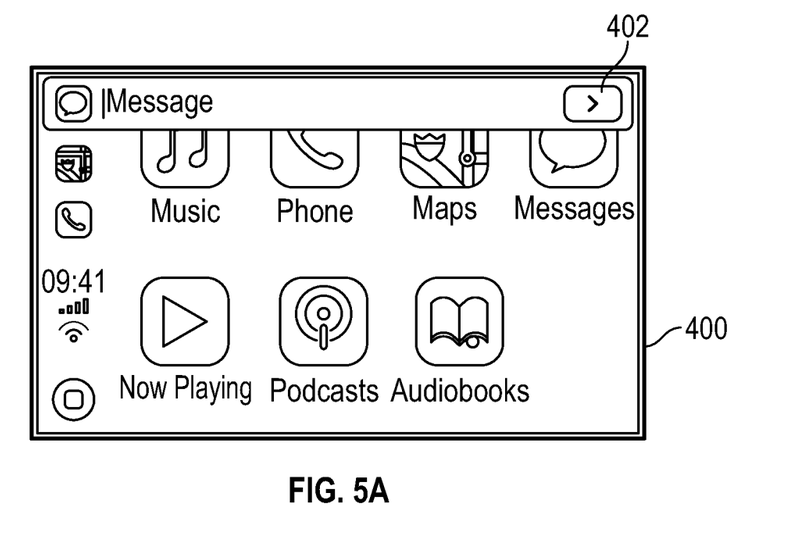
FIG. 5A illustrates overlapping information on an in-vehicle display and the identification of a focusing point on the display in accordance with an exemplary embodiment.
Figure 5B:
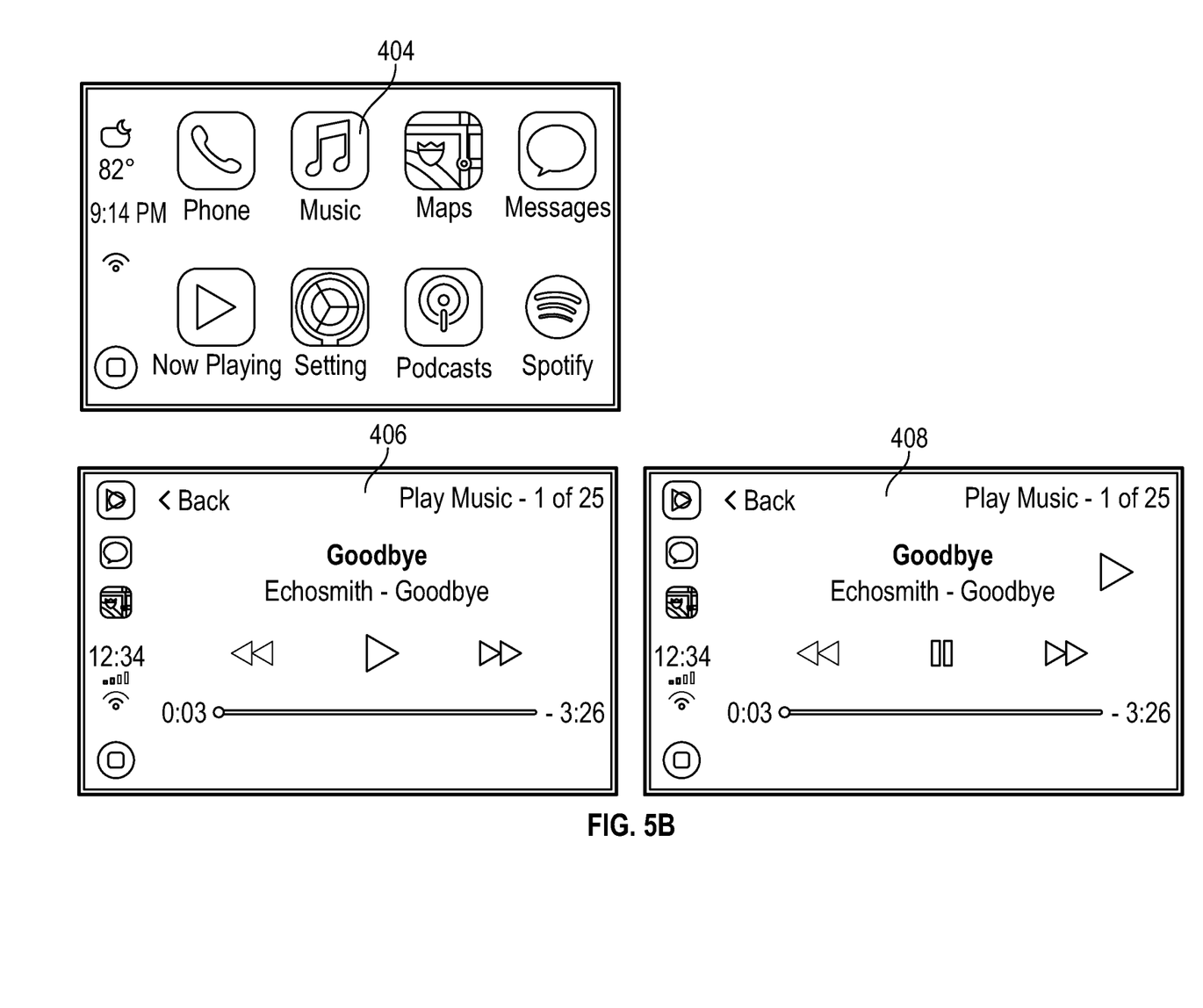
FIG. 5B illustrates two alternative information at the same location in accordance with an exemplary embodiment.
Figure 5C:
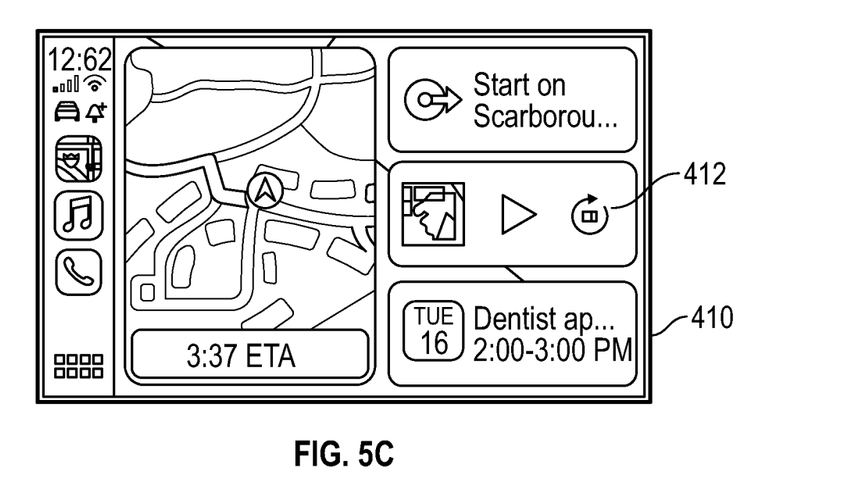
FIG. 5C illustrates information at a different location than that shown in FIG. 5B.

FIGS. 5A-5C illustrate another use of the system 100. In FIG. 5A, two overlapping pieces of information are presented to the person 12. The person 12 is able to check the new message by focusing on the arrow 402, even though it is partially overlapped with the "Messages" icon in the display 400.

In FIG. 5B, the person 12 visually focuses on the music icon 404. In response the system presents to the person 12, two information images 406 and 408. As such, the person 12 is able to pause 408 or play 406 the music by merely focusing on the pause or play buttons. Thus, the system 100 is able to identify the two buttons even if they are in the same location. In FIG. 5C, the play button 412 is displayed on a different interface 410. The system 100, however, allows the person 12 to identify the play button at a different location.

In various arrangements, the BCI device 104 is combined with an eye tracker. As another source of input, the BCI device helps calibrate the eye tracker and helps improve eye tracking data (e.g., reduce false alarms in DMS data). The BCI device 104 is sensitive to slight changes in size, so that it is able to identify visual recognition of 3D objects in the distance, which can be validated by the eye tracker and vehicle sensors (e.g., a camera).

A system of the present disclosure offers several advantages. These include

Easy Synchronization: That is, there is no need to synchronize the BCI signals with a particular scene, as the scene itself is part of BCI recognition. In contrast, eye tracking data itself is meaningless unless the coordinates can be synchronized with different scenes in real time.

Less noise: Human eyes have three main visual fields: fovea, parafovea, and peripheral with interactions between these fields. The system 100 eliminates or minimizes the noise that, otherwise, would be too noisy to tell which object that the person is looking at.

Discrimination between unintentional gaze and intentional staring. The system 100 recognizes the person's focus and offers intentional control.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A system for interfacing a motor vehicle with a person residing in the motor vehicle, the system comprising:
    a brain-computer interface (BCI) configured to monitor a brain activity of the person, wherein the brain activity is in the form of electric signals from a visual cortex of the person;
    a driver monitoring system (DMS) configured to collect data on where the person is looking, wherein the DMS includes a camera; and
    an electronic control unit (ECU) in communication with the BCI and the DMS, wherein the ECU includes a processor and a non-transitory computer readable medium, the ECU is programmed to control a head-up display (HUD) of the motor vehicle based on the brain activity of the person monitored by the BCI and the data on where the person is looking received from the DMS; and
    wherein the ECU is programmed to:
        determine a visual focus strength of the person on an in-vehicle display of the motor vehicle;
        determine a visual focus duration of the person on the in-vehicle display of the motor vehicle;
        compare the visual focus strength of the person on an in-vehicle display of the motor vehicle with a strength threshold to determine whether the visual focus strength of the person on an in-vehicle display of the motor vehicle is greater than the strength threshold;
        compare the visual focus duration of the person on the in-vehicle display of the motor vehicle with a duration threshold to determine whether the visual focus duration of the person on the in-vehicle display of the motor vehicle is greater than the duration threshold; and
        in response to determining that: (a) the visual focus strength of the person on an in-vehicle display of the motor vehicle is greater than the strength threshold and (b) the visual focus duration of the person on the in-vehicle display of the motor vehicle is greater than the duration threshold, command the in-vehicle display to execute a command.

2. The system of claim 1, wherein the DMS determines if the person is looking at the HUD or information on the HUD.

3. The system of claim 2, wherein the system differentiates what the person sees and does not see on the HUD, or even looking at the HUD.

4. The system of claim 2, wherein the system recognizes that the person has seen information on the HUD and replaces the information with other useful information on the HUD and a screen display.

5. The system of claim 4, wherein the system enables the person to access controls on the screen display or the HUD by looking at the HUD or the screen display.

6. The system of claim 1, wherein the system monitors a fatigue of the person.

7. The system of claim 6, wherein the ECU is programmed to:
    determine a fatigue level of the person using a following equation:

$$f = \frac{t-T}{l-L} \cdot \frac{L}{T}$$

where:
        f is the fatigue level of the person;
        t is a time required to complete a command execution;
        T is a duration of the visual focus of the person;
        l is an average strength level of the visual focus of the person during the of the visual focus of the person;
        L is a minimum visual focus strength level required to complete the command execution;
    determine whether the fatigue level is greater than a fatigue level threshold; and
    in response to determining that the fatigue level is greater than the fatigue level threshold, send a notification to the person.

8. The system of claim 1, wherein the BCI is integrated into a headpiece.

9. The system of claim 1, wherein the system provides visual, auditory or tactile information to the person.

10. A method for interfacing a motor vehicle with a person residing in the motor vehicle, the method comprising:
    receiving, via a brain-computer interface (BCI), electric signals from a visual cortex of the person, wherein the electrical signals from the visual cortex of the person is indicative of a brain activity of the person;
    receiving, via a driver monitoring system (DMS), data on where the person is looking;
    controlling, via an electronic control unit (ECU), a head-up display (HUD) of the motor vehicle based on electrical signals from the visual cortex of the person and the data on where the person is looking to enable the system to execute operations; and
    determining a fatigue level of the person using a following equation:

$$f = \frac{t-T}{l-L} \cdot \frac{L}{T}$$

where:
        f is the fatigue level of the person;
        t is a time required to complete a command execution;
        T is a duration of a visual focus of the person;
        l is an average strength level of the visual focus of the person during the of the visual focus of the person;
        L is a minimum visual focus strength level required to complete the command execution;
    determining whether the fatigue level is greater than a fatigue level threshold; and
    in response to determining that the fatigue level is greater than the fatigue level threshold, sending a notification to the person.

11. The method of claim 10, further comprising determining if the person is looking at the HUD or information on the HUD.

12. The method of claim 11, further comprising differentiating what the person sees and does not see on the HUD, or even looking at the HUD.

13. The method of claim 11, further comprising recognizing that the person has seen information on the HUD and replaces the information with other useful information on the HUD and a screen display.

14. The method of claim 13, further comprising enabling the person to access controls on the screen display or the HUD by looking at the HUD or the screen display.

15. The method of claim 10, furthering comprising monitoring the fatigue of the person.

16. The method of claim 15, wherein the fatigue of the person is determined by the visual focus strength and duration of the person.

17. The method of claim 10, wherein the BCI is integrated into a headpiece.

18. The method of claim 17, wherein the headpiece is a headphone, a cap in a headrest of a seat, or in the seat itself.

19. A system for interfacing a motor vehicle with a person residing in the motor vehicle, the system comprising:
- a brain-computer interface (BCI) configured to monitor brain activity from the person, wherein the brain activity is in the form of electric signals from a visual cortex of the person;
- a driver monitoring system (DMS) configured to collect data on where the person is looking, wherein the DMS includes a camera, wherein the DMS is configured to determine if the person is looking at a head-up display (HUD) of the motor vehicle to enable the person to access controls on a screen display or the HUD by looking at the HUD or the screen display; and
- wherein the system is configured to provide visual, auditory or tactile information to the person; and
- wherein the system further includes an electronic control unit (ECU) in communication with the BCI and the DMS, the ECU includes a processor and a non-transitory computer readable medium, the ECU is programmed to control a head-up display (HUD) of the motor vehicle based on the brain activity of the person monitored by the BCI and the data on where the person is looking received from the DMS;

wherein the ECU is programmed to:
- determine a visual focus strength of the person on an in-vehicle display of the motor vehicle;
- determine a visual focus duration of the person on the in-vehicle display of the motor vehicle;
- compare the visual focus strength of the person on an in-vehicle display of the motor vehicle with a strength threshold to determine whether the visual focus strength of the person on an in-vehicle display of the motor vehicle is greater than the strength threshold;
- compare the visual focus duration of the person on the in-vehicle display of the motor vehicle with a duration threshold to determine whether the visual focus duration of the person on the in-vehicle display of the motor vehicle is greater than the duration threshold; and
- in response to determining that: (a) the visual focus strength of the person on an in-vehicle display of the motor vehicle is greater than the strength threshold and (b) the visual focus duration of the person on the in-vehicle display of the motor vehicle is greater than the duration threshold, command the in-vehicle display to execute a command.

* * * * *